(12) United States Patent
Roth et al.

(10) Patent No.: US 10,458,987 B2
(45) Date of Patent: Oct. 29, 2019

(54) TUMOR ENERGY METABOLISM PROFILING

(71) Applicant: UNIVERSITÄT HEIDELBERG, Heidelberg (DE)

(72) Inventors: Wilfried Roth, Schwetzingen (DE); Georg Gdynia, Heidelberg (DE); Sven Sauer, Mannheim (DE)

(73) Assignee: UNIVERSITÄT HEIDELBERG, Heidelberg (DE)

( * ) Notice: Subject to any disclaimer, the term of this patent is extended or adjusted under 35 U.S.C. 154(b) by 0 days.

(21) Appl. No.: 14/898,456

(22) PCT Filed: Jul. 2, 2014

(86) PCT No.: PCT/EP2014/064100
§ 371 (c)(1),
(2) Date: Dec. 14, 2015

(87) PCT Pub. No.: WO2015/000980
PCT Pub. Date: Jan. 8, 2015

(65) Prior Publication Data
US 2016/0146816 A1    May 26, 2016

(30) Foreign Application Priority Data
Jul. 4, 2013  (EP) .................................. 13175028

(51) Int. Cl.
*C12Q 1/00*  (2006.01)
*G01N 33/574*  (2006.01)
*G01N 33/573*  (2006.01)

(52) U.S. Cl.
CPC ......... *G01N 33/573* (2013.01); *G01N 33/574* (2013.01); *G01N 33/57484* (2013.01); *C12Q 1/00* (2013.01); *G01N 2333/90* (2013.01); *G01N 2333/904* (2013.01); *G01N 2333/90206* (2013.01); *G01N 2333/90216* (2013.01); *G01N 2333/91215* (2013.01); *G01N 2800/50* (2013.01); *G01N 2800/52* (2013.01); *G01N 2800/54* (2013.01); *G01N 2800/7028* (2013.01); *G01N 2800/7066* (2013.01)

(58) Field of Classification Search
None
See application file for complete search history.

(56) References Cited

PUBLICATIONS

International Search Report and the Written Opinion of International Application No. PCT/EP2014/064100 dated Sep. 16, 2014.
Gonzalez Buitrago J M et al., "Cytoplasmic Enzyme Activities in Human Hypernephroma Compared With Normal Renal Cortical Tissue", *Urologia Internationalis*, vol. 43, No. 1, Jan. 1, 1988 (Jan. 1, 1988), pp. 32-34, XP009174411, ISSN: 0042-1138, the whole document.
Ross C et al., "Quantitative biochemical analysis of samples from squamous cellcarcinoma", *Otolaryngology and Head and Neck Surgery*, Roch Ester, US, vol. 119, No. 5, Nov. 1, 1998 (Nov. 1, 1998), pp. 455-459, XP027449494, ISSN: 0194-5998, DOI: 10.1016/S0194-5998(98)70101-9 [retrieved on Nov. 1, 1998] the whole document.
Gumustas, K et al., "Cytochrome oxidase activity and ATP levels in high-grade gliomas and meningiomas", *Turkish Neurosurgery: Official Publication of Turkish Neurosurgical Society, Turkish Neurosurgical Society*, TR, vol. 16, No. 2, Jan. 1, 2006 (Jan. 1, 2006), pp. 64-68, XP009174415, ISSN: 1019-5149, Retrieved from the Internet: URL:http://www.turkishneurosurgery.org.tr/, pdf/pdfJTN 77.pdf, the whole document.

*Primary Examiner* — Robert J Yamasaki
*Assistant Examiner* — Charles Zoltan Constantine
(74) *Attorney, Agent, or Firm* — M. J. Ram and Associates; Michael J. Ram

(57) ABSTRACT

A diagnostic method for the prediction of tumor prognosis including the likelihood of formation of metastases or of relapse or local recurrence in tumor related diseases in a mammal and the provision of a therapy recommendation for a patient the enzyme activity of key enzymes of the energy metabolism is determined in fresh tumor tissue or fresh tumor cell mass after 24 hours incubation in a cell culture medium. Incubation reduces nutrition, drug and biopsy/surgery effects on the energy metabolism of the tissue slices or the cell mass. The quotients of enzyme activity of anaerobic enzymes are put in ratio to the enzyme activity of aerobic enzymes or vice versa. Said ratio can be taken into account for prognosis of metastasis and a therapy recommendation.

24 Claims, 2 Drawing Sheets

TUMOR ENERGY METABOLISM PROFILING

FIELD OF THE INVENTION

The invention refers to a diagnostic method for the prognosis of tumor progression (including the prediction of the likelihood of occurrence of metastases and relapse) in tumor related diseases in a mammal and the provision of a therapy recommendation for the patient. It further describes the use of enzyme activities of key enzymes in energy metabolism for a decision on an individualized tumor therapy.

BACKGROUND OF THE INVENTION

The consideration of individual parameters of the cellular energy metabolism for the evaluation of the potential of metastasis of malignant tumors has often been tested, however without transferring test results or test procedures into clinical every day life (*Novartis Foundation symposium* 240, 251 (2001)). The concentration of substrates and products of the energy metabolism such as glucose, glutamine, ketone bodies, lactate and ATP have been determined in cell lines in xenograft tumors, in cryo tissue samples of tumor patients and also in vivo in larger vessels supplying a tumor (Cancer research 62, 6674 (Nov. 15, 2002)). These determinations are based on methods which are generally known in the analysis of metabolism such as enzyme activity tests, bioluminescence tests, NMR or mass spectrometry. Presently, there is no clinical test in which all essential energy metabolism pathways in tumor tissue are tested to give evidence about an individual prognosis of a tumor or about the chemosensitivity of a tumor.

Several published experimental approaches for an application of enzyme activity tests of energy metabolism enzymes have not been considered in clinical therapy of human malignant tumors in spite of the fact that these enzyme activities are different in healthy and tumor tissue. Determination methods are necessary which allow a quick decision on a therapy and which allow a reliable prognosis of the tumor development after tumor diagnosis. The presently available methods for analysis of the energy metabolism of malignant tumors do not fulfill the aforementioned requirements.

It would be highly beneficial if such methods that are performed at tissue samples—herein the term "tissue samples" comprises solid tissue and single cells from liquid material (i.e. blood)—would both provide results that are identical to those in vivo of a patient and allow an interindividual cross-comparison of the measured enzyme activities. This is not possible with an analysis of formalin-fixed tissue, cell lines, spheroids and xenograft tumors. A representation of the energy metabolism in vivo could be a cryo tissue sample taken from biopsy material. Such samples allow the determination of metabolites; the determination of activities of enzymes that are located in cell compartments or are part of multienzyme complexes is limited. However, measurements in cryo tissue have the disadvantage that individual differences of patients in energy and substrate supply prior to taking the biopsy material from a patient and the changes in tumor metabolism induced by the surgeon during the biopsy have an influence on the enzyme activity. Such circumstances do not allow standardization and interindividual cross-comparison of measured metabolic data. Already the duration of the biopsy, the kind and the dosage of a narcotic during biopsy or drug administration may distinctly influence energy metabolism in a cell (Resuscitation 19, 159 (April 1990)).

Other methods in which the expression of enzymes of the energy metabolism in patient tissue is determined via immunohistochemistry or bioluminescence are semiquantitative and do not indicate the actual activity of the enzymes. *Nature Chemical Biology* 1 130 (August 2005) describes the so-called "activity-based-proteome-profiling" or its further developed application (click-chemistry) that show active enzymes in homogenates and living tissue; however, they are semiquantitative, very time consumptive and costly.

Up to now, none of the aforementioned methods or combination of such methods allows the determination or representation of the complete energy metabolism of living tumor tissue. In particular, the activity of key enzymes involved in the metabolism of all known relevant cellular energy substrates has not yet been considered and determined for a prognosis of tumor progression or for a therapy recommendation.

SUMMARY OF THE INVENTION

The problem underlying the invention is to provide a diagnostic method for the prognosis of tumor progression, including the prediction of the likelihood of occurence of metastases (in lymph nodes and/or at distant sites) and relapse and the provision of a therapy recommendation. The diagnosis method shall be easy enough for clinical everyday life.

This problem is solved with a diagnostic method for the prediction of tumor prognosis including the likelihood of formation of metastases, relapse occurrence, and/or local recurrence and the provision of a therapy recommendation comprising the steps of (a) incubation of a tumor patient's sample material and a comparative sample material from the patient in a culture medium to allow elimination of nutrition, drug and biopsy effects on the energy metabolism in the sample materials;

(b) preparation of a cell homogenate and sub cellular fractions from the sample materials of step (a);

(c) determination of enzyme activities of at least one anaerobic and at least one aerobic key enzyme of the energy metabolism of the cell homogenate or the subcellular fraction and determination of a quotient of the enzyme activity of an enzyme determined in the sample material and the comparative sample material;

(d) calculation of the ratio of anaerobic to aerobic energy gain or vice versa based on the quotient determined in step (c) in the sample material and the comparative sample material, wherein the patient sample material is selected from tissue slices, tumor cell mass and isolated cells and the comparative sample material is selected from a tumor distant tissue slice or a material which in step (a) is incubated under conditions to up regulate the anaerobic energy metabolism and is selected from a tumor tissue slice, tumor cell mass and isolated cells.

The ratio mentioned in step (d) above can also be calculated as the ratio of aerobic to anaerobic energy gain; or in other words the reciprocal value of the ratio defined in step (d) above. The method described herein uses the absolute deviation of the above mentioned ratio from a normal value that is tumor distant and tumor tissue do not differ in anaerobic and aerobic energy metabolism.

According to another aspect of the invention, the invention is directed to the use of the ratio of the enzyme activity of at least one anaerobic enzyme and at least one aerobic enzyme of the key enzymes of the energy metabolism determined (i) in tumor tissue and for comparison in tumor distant tissue or (ii) in tumor tissue or tumor cells and for comparison under anoxic condition as a marker or a biomarker for the prediction of tumor prognosis including the likelihood of formation of metastases, relapse occurrence, and/or local recurrence.

Important features of the invention are that the patient samples used in the method of the invention are fresh patient (tumor) samples. Before determination of enzyme activity the patient samples are incubated for a longer period of time. Finally, an energy profile of the tumor is provided that is used for prognosis.

However, it is also possible and feasible to analyze cryoconserved tumor tissue or a cryoconserved tumor cell mass with the herein described analytical method. In this case it is important that the tissue or cell mass was stored at temperatures where the enzymatic activity of the material very substantially slows, accepted are ranges below −130° C., preferred is the storage at −196° C. in liquid nitrogen ($LN_2$).

DETAILED DESCRIPTION

Figure 1:
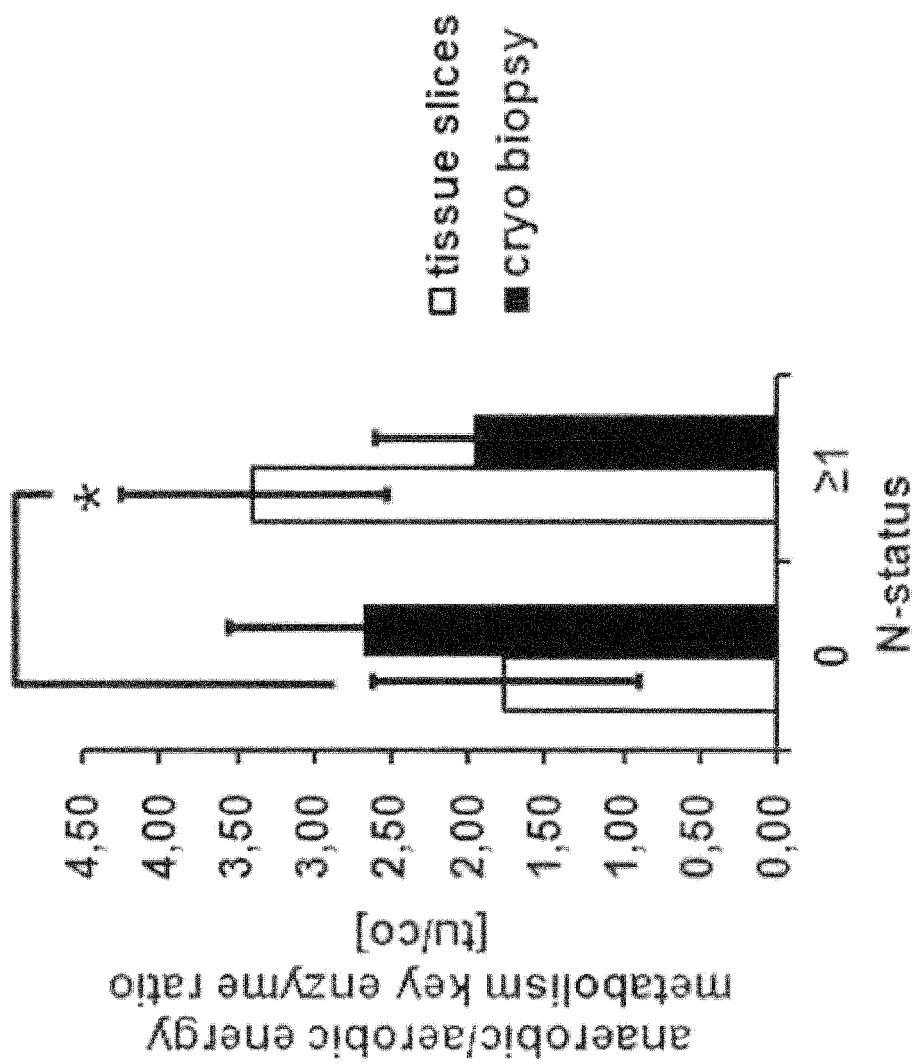
FIG. 1 is a graphical representation of a first Example comparing key enzyme ratios for anaerobic/aerobic energy metabolism in tissue slices and cryobiopsy samples.

Subsequently, the embodiments of the method of the invention as described are explained in more detail. Hence, the aforementioned problem is solved with a first method of the invention comprising the steps of
(a) incubation of a fresh tissue slice taken from a sample of a tumor tissue and of a tumor distant tissue of a patient in a cell culture medium to reduce nutrition, substrate, drug and biopsy effects on the energy metabolism of the tissue slice;
(b) preparation of a cell homogenate and subcellular fractions and from the tissue slices of step (a),
(c) determination of enzyme activities of at least one key enzyme of anaerobic energy metabolism and at least one of aerobic energy metabolism in the cell homogenate and/or in the subcellular fraction in the tumor tissue and in the tumor distant tissue and formation of a quotient of the enzyme activity of an enzyme determined in tumor tissue and in tumor distant tissue;
(d) calculation of the ratio of anaerobic to aerobic energy gain based on the quotient determined in step (c) in tumor tissue and tumor distant tissue.

The provision of a prognosis and a therapy recommendation is possible on the basis of an enzyme activity profile obtained in step (d).

The ratio mentioned in step (d) above can also be calculated as the ratio of aerobic to anaerobic energy gain; or in other words the reciprocal value of the ratio defined in step (d) above. The method described herein uses the absolute deviation of the above mentioned ratio from a normal value that is tumor distant and tumor tissue do not differ in anaerobic and aerobic energy metabolism.

The invention is further directed to a second diagnostic method for the prognosis of tumor progression, including the prediction of likelihood of occurrence of metastasis and relapse and the provision of a therapy recommendation in which no biopsy material distant from a tumor is used for comparative or reference purposes. This diagnostic method does only use tumor tissue samples. Thus, this method is an alternative method to the first method of the invention. Hence, the invention is also directed to a diagnostic method comprising the steps of
(a) incubation of a fresh tissue slice taken from a biopsy material of a tumor tissue of a patient or tumor cell mass of a patient in a cell culture medium to reduce nutrition, substrate, drug and biopsy effects on the energy metabolism of the tissue slices;
(b) incubation of a second tissue slice from the same biopsy material under conditions to upregulate the anaerobic energy metabolism in the tissue slice;
(c) preparation of a cell homogenate and subcellular fractions from the tissue slices of step (a) and (b),
(d) determination of enzyme activity of at least one anaerobic and at least one aerobic key enzyme of the energy metabolism of the cell homogenate and/or the subcellular fraction in the tumor tissue and in the tumor tissue sample with the up regulated anaerobic energy metabolism obtained in step (c) and determination of a quotient of the enzyme activity of an enzyme in the tumor tissue and in the tumor tissue sample with the up regulated anaerobic energy metabolism;
(e) calculation of the ratio of anaerobic to aerobic energy gain based on the quotient determined in step (c) in tumor tissue and in the tumor tissue sample with the up regulated anaerobic energy metabolism.

The provision of a prognosis and a therapy recommendation is possible on the basis of an enzyme activity profile obtained in step (e).

The ratio mentioned in step (e) above can also be calculated as the ratio of aerobic to anaerobic energy gain; or in other words the reciprocal value of the ratio defined in step (e) above. The method described herein uses the absolute deviation of the above mentioned ratio from a normal value that is tissue slices cultivated under conditions described in (a) and (b) do not differ in anaerobic and aerobic energy metabolism.

Subject matter of a third embodiment of the invention is a third method which starts with tumor cell mass collected from a patient in which the enzyme activities are determined. This third diagnostic method of the invention comprises the steps of
(a) incubation of a part of fresh tumor cell mass taken from a patient in a cell culture medium to allow the elimination of drug, nutrition, substrate and biopsy effects on the energy metabolism;
(b) incubation of the other part of the tumor cell mass taken from the patient under conditions to up regulate the anaerobic energy metabolism;
(c) preparation of sub cellular fractions and a cell homogenate from the tumor cell mass of steps (a) and (b),
(d) determination of the enzyme activity of at least one anaerobic and at least one aerobic key enzyme of the energy metabolism of the sub cellular fraction or the cell homogenate in the tumor cell mass of step (a) and in the tumor cell mass with the up regulated anaerobic energy metabolism and determination of a quotient of the enzyme activity of an enzyme in the tumor cell mass and in the tumor cell mass with the up regulated anaerobic energy metabolism;

(e) calculation of the ratio of anaerobic to aerobic energy gain based on the quotient determined in step (d) in tumor cell mass and in the tumor cell mass with the up regulated anaerobic energy metabolism.

The ratio mentioned in step (e) above can also be calculated as the ratio of aerobic to anaerobic energy gain; or in other words the reciprocal value of the ratio defined in step (e) above. The method described herein uses the absolute deviation of the above mentioned ratio from a normal value that is tissue slices cultivated under conditions described in (a) and (b) do not differ in anaerobic and aerobic energy metabolism.

In a fourth embodiment of the invention the diagnostic method for the prediction of tumor prognosis including the likelihood of formation of metastases, relapse occurrence, and/or local recurrence and the provision of a therapy recommendation comprising the steps of (a) isolation of cells from a solid or liquid tumor sample taken from a patient, estimation of the number of isolated cells, dilution of these cells and incubation of these cells in a cell culture medium to allow elimination of drug, nutrition and biopsy effects on the energy metabolism and to allow proliferation of the cells;

(b) incubation of the same amount of cells that were isolated and treated like described in (a) under conditions to up regulate the anaerobic energy metabolism;

(c) preparation of sub cellular fractions and a cell homogenate from the isolated cells of step (a) and (b);

(d) determination of enzyme activity of at least one anaerobic and at least one aerobic key enzyme of the energy metabolism of the sub cellular fraction or the cell homogenate in the isolated cells and in the isolated cells with the up regulated anaerobic energy metabolism and determination of a quotient of the enzyme activity of an enzyme in the isolated cells of (a) and in isolated cells with the up regulated anaerobic energy metabolism;

(e) calculation of the ratio of anaerobic to aerobic energy gain or vice versa based on the quotient determined in step (d) in the isolated cells of step (a) and in the isolated cells with the up regulated anaerobic energy metabolism.

The methods of the invention are ex vivo and in-vitro methods.

In the first method of the invention the activity of key enzymes relevant in energy providing pathways of a cell are measured. The enzyme activities are measured in a tumor tissue slice and in a tissue slice of a tissue distant from the tumor. The enzymes are involved in the anaerobic and aerobic energy gain of the cell. For an enzyme the quotient of enzyme activity in the tumor tissue slice and in the tumor distant tissue slice is formed. From the quotients of enzyme activities of enzymes involved in the aerobic energy gain and of enzymes involved in the anaerobic energy gain an energy profile is, calculated. The energy profile allows a prediction on prognosis of the tumor and the selection of an individual therapy for a patient.

The second method of the invention is suited for all measurements taken from tumor tissue or tumor cells to which no corresponding normal tissue (cancer free tissue) or no corresponding normal cells (cancer free cell mass/non-cancerous cells) can or could be obtained. For example, in case of a prostate cancer, macroscopically it is very difficult to differentiate during biopsy between tumor and tumor free tissue. Further, the tumor can be distributed over the complete organ or the complete structure (lymph node), thus making it impossible to obtain tumor free tissue. Further cases that can be considered are those where the corresponding normal tissue cannot be identified any longer (CUP—cancer of unknown primary syndrome). Finally this alternative method of the invention is suited for cancer tumor diseases without a solid tumor and where tumor cells are mixed with non-neoplastic cells, making it difficult to obtain normal cells as a reference for the measurement. In particular, this will be the case in hematologic tumor diseases.

The third method of the invention uses tumor cell mass instead of a tissue slice. This is important for a tumor which is not solid. These are tumours where the tumor cells are in liquid suspension. This is for example the case in blood cancers.

The fourth embodiment of the invention uses isolated cells from a tumor sample instead of a tissue slice or instead of a high number (up to $5 \times 10^6$ cells) of tumor cells. In case of solid tumor samples this is important for a tumor sample that is too small to be cut precisely. In case of liquid tumor samples this is important for a tumor sample that contains a very low number of cells. In both cases this is important to achieve a low limit of detection (LOD). For this purpose cells are isolated from the solid tumor samples by standard methods (e.g. enzymatic digestion), then diluted in cell culture medium and seeded into cell culture plates (e.g. 96-well cell culture plates). The isolated cells are allowed to proliferate for up to two weeks. Cells isolated from a liquid tumor sample are treated the same way; however, the isolation step is performed by centrifugation. Then the aforementioned measurements are performed. In case of omitting the cell proliferation step due to a desired acceleration of the method, detection of the enzyme activities can be amplified using fluorescent or fluorogenic enzyme substrates or other amplifying methods known to the skilled in the art. In particular, this modified method could be important when measuring needle biopsy (including stereotactic needle biopsy) material, for example from the prostate (e.g. prostate cancer), the liver (e.g. hepatocellular carcinoma), the skin (e.g. malignant melanoma), the brain (e.g. glioblastoma or medulloblastoma) or cerebrospinal fluid (e.g. containing malignant brain tumor cells).

The method of the invention is suited for all kinds of tumors that are known to form metastasis or local recurrence.

The measurement of enzyme activities and the sample preparation in the method of the invention fulfills the requirements of a feasible and cost effective clinical test. The result of the method of the invention improves the decision on therapy and prognosis of malignant tumor diseases. In contrast to the known methods of determining enzyme activities in cryo biopsies which at best only allow for differing between tumor tissue and non-tumor tissue in one patient, the method of the invention allows a comparison of data obtained from a group of different patients. This supports safety for the selection of a therapy suited for a patient.

With the method of the invention a complete metabolic energy profile of a respective tumor is established on the basis of the enzyme activities of key enzymes of the cellular energy metabolism. Due to its standardization this method allows a quick performance and is suited for application in clinical everyday life to determine a complete and individual energy profile of the tumor of a patient. The process of the invention allows an interindividual cross-comparison of the parameters because of the standardized controlled energy metabolism in the processed samples.

An increasing anaerobic energy metabolism in the tissue slices determined according to the methods of the invention significantly correlates with the tumor progression. Thus, it is the ratio of anaerobic to aerobic energy gain which is predictive for the likelihood of metastasis, relapse or local recurrence. A small number of tumor subgroups, such as Hodgkin's lymphomas could show a stronger dependence on aerobic energy metabolism. The method of invention is also suitable for these cases since it detects an increase of anaerobic over aerobic energy metabolism and vice versa.

In the method of the invention a metabolic profile of a specific tumor is established on the basis of enzyme activities of key enzymes of the cellular energy metabolism. The essential finding of the invention is to establish at a metabolically active ex vivo tumor tissue an energy profile of all relevant energy providing metabolic pathways of the cell.

The enzymes which may be considered in the method of the invention are key enzymes in human anaerobic and aerobic energy providing metabolic pathways. These pathways include essentially the glycolysis, glutaminolysis, lipolysis, the citric cycle and the oxidative phosphorylation (mitochondrial respiration).

Key enzymes of the energy metabolism of the cell and tumor cell suited for the methods of the invention include malic enzyme (ME), in particular ME1, lactate dehydrogenase (LDH), pyruvate kinase low affinity (PKLA; preferably dimeric PK-M2), pyruvate kinase high affinity (PKHA; preferably tetrameric PK-M2), hexokinase and cytochrome c oxidase (COX). These are enzymes which are present in the human body. They are present in healthy tissue and in tumor tissue. The specific enzyme activity is expressed in U/mg protein. Of these enzymes malic enzyme (ME), lactate dehydrogenase (LDH), pyruvate kinase low affinity (PKLA or dimeric PK-M2) and hexokinase are considered the enzymes of anaerobic energy metabolism whereas pyruvate kinase high affinity (PKHA; tetrameric PK-M2) and cytochrome c oxidase (COX) are considered the enzymes of aerobic energy metabolism.

The malic enzyme (malate decarboxylating enzyme) is a key enzyme of glutaminolysis. The glutaminolysis comprises a series of biochemical reactions in which the amino acid glutamine is degraded to glutamate, aspartate, $CO_2$, pyruvate, lactate, alanine and citrate. Energy can be provided in this pathway anaerobically. In particular, the malic enzyme catalyzes the reversible chemical reaction:

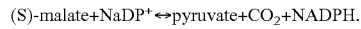
(S)-malate+NaDP$^+$↔pyruvate+$CO_2$+NADPH.

Lactate dehydrognase (LDH) catalyses the last reaction step in the anaerobic glycolysis and in the anaerobic glutaminolysis:

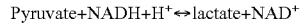
Pyruvate+NADH+H$^+$↔lactate+NAD$^+$

Thus, L-lactate dehydrogenase is the enzyme which catalyses the oxidation of L-lactate to pyruvate and concurrently the reduction of NAD$^+$ to NADH/H$^+$ as well as its back reaction.

The pyruvate kinases PKLA (pyruvate kinase low affinity, for example dimeric PK-M2) and PKHA (pyruvate kinase high affinity, for example tetrameric PK-M2) are enzymes that are involved in glycolysis. They catalyze the transfer of a phosphate group from phosphoenolpyruvate to ADP, yielding one molecule of pyruvate and one molecule of ATP. Thus, PKLA activity provides information on the anaerobic branch of glycolysis. In contrast, PKHA activity provides information on the aerobic branch of glycolysis.

Hexokinase catalyzes the phosphorylation of glucose to glucose-6-phosphate in the presence of ATP and Mg$^{2+}$ ions. Besides glucose-6-phosphate ADP and H$^+$ are obtained.

Measurement of cytochrome c oxidase (COX) activity provides information on oxidative phosphorylation, i.e. mitochondrial oxygen consumption. It is the last enzyme in the respiratory electron transport chain in the mitochondrial membrane. For the determination of enzyme activity of cytochrome c oxidase reduced cytochrome c is oxidized.

Further, as a marker for beta oxidation, i.e. the metabolism of fatty acids, mitochondrial acyl-CoA dehydrogenases, e.g. palmitoyl-CoA dehydrogenase (very long chain acyl-CoA dehydrogenase) can be used. Energy production from beta oxidation occurs via citric cycle and/or mitochondrial respiratory chain, there it is considered as a pathway of anaerobic energy production.

In a preferred embodiment of the invention the enzyme activity of at least one anaerobic enzyme and the enzyme activity of at least one aerobic enzyme is determined and taken into account for the formation of the quotient. Thus, for the purpose of the invention one may determine the activity of one or more of the enzymes selected from malic enzyme (ME), lactate dehydrogenase (LDH), pyruvate kinase low affinity (PKLA or dimeric PK-M2), hexokinase and an acyl-CoA dehydrogenase as enzyme of anaerobic energy metabolism and the activity of one or more of the enzymes selected from pyruvate kinase high affinity (PKHA; tetrameric PK-M2) and cytochrome c oxidase (COX) as enzymes of aerobic energy metabolism. The determined activities serve to form the quotient as defined before.

It is also possible that the number of anaerobic and aerobic enzymes determined in the method of the invention is different.

In a further preferred embodiment of the invention the ratio of the relatively easy detectable (that means with known relatively high specific activities) enzymes, PKLA, LDH and PKHA is determined. The determination of these enzymes might be in particular feasible for daily laboratory routine using the herein described analytical method.

In a further preferred embodiment of the invention at least the enzyme activity of malic enzyme and at least one enzyme of the anaerobic as well as of the aerobic energy production is determined and taken into account for the formation of the ratio. According to a further preferred embodiment of the invention the enzyme activities taken into account are those of the enzymes ME1, COX, PKHA, PKLA and LDH.

The relation (ratio) of anaerobic to aerobic generation of energy determined in a tissue sample allows a prognosis on the progression of a tumor. In particular, the increasing anaerobic energy metabolism in tissue slices correlates significantly with the tumor progression.

For the tissue sample preparation a biopsy or a resection of parenchyma and/or connective tissue (containing the tumor) is performed at a patient. A variety of biopsy and operation techniques can be applied for this purpose. These techniques are known and widely used since many years. In one of the methods of the invention samples are taken from the tumor tissue and a healthy tissue belonging to the same organ which is referred to in the invention as tumor distant tissue. This is important because the enzyme activity of an enzyme both in tumor tissue and in healthy tissue can be considered. Thus, a tumor distant tissue can be a tissue which is taken from a place adjacent to the tumor but which is not part of the tumor. Most preferable the tumor distant tissue should belong to the parenchyma or connective tissue where the tumor originated in.

The sample or biopsy material or cell mass which is subjected to a method of the invention is a fresh material. Fresh means that the tissue material or cell mass has not been subjected to freezing or formalin fixation. The sample or biopsy material is added to a cell culture medium and is transferred to an instrument in which the sample or biopsy material can be processed to thin tissue slices. It is an essential feature of the methods of the invention that the tissue slice is taken from freshly obtained tissue. Thus neither the original tumor tissue nor the tissue slice is conserved or is frozen or is treated with a gelling material such like agarose.

Preferably the thickness of the tissue slice is selected to allow diffusion of nutrients from the cell culture medium into the interior of the tissue slice. Further the thickness of the tissue slice should be selected to maintain the metabolic performance of the sliced tissue during incubation. Hence, the thickness of the tissue slice can be 200 µm to 400 µm, preferable 250 µm to 350 µm and most preferably about 300 µm.

The apparatus for sectioning of the fresh biopsy material can be a tissue slicer. A tissue slicer for the preparation of tissue slices is available from Leica Microsysteme Vertrieb GmbH, 35578 Wetzlar. For example, the Leica VT 1200S Vibratome® blade microtome is suited for the purpose of obtaining tissue slices for the methods of the invention. Also suited is a tissue chopper available from Leica Microsysteme Vertrieb GmbH and the McIlwain tissue chopper from Campden Instruments, Ltd., Loughborough, Leics, UK. A so-called tissue chopper allows for a quicker preparation of the tissue slices.

It is an essential feature of the invention that the tissue slices are incubated in a cell culture medium for a certain period of time. This incubation allows degradation or metabolisation of drugs in the tissue slices given to the patient before the biopsy is taken and to eliminate biopsy effects on the energy metabolism of the tissue slices induced by the surgery or by the patient's body, e.g. the patient's nutrition status, medication or chronic diseases. During the incubation the tissue slices recover from nutrition, drug and surgery effects on the tissue. After the incubation of the tissue slices such effects on the tissue slice should be removed. After the incubation of the tissue slices according to the invention nutrition, medication or surgery effects shall not have any influence on the enzyme activity of the key enzymes in energy metabolism of the tissue slices. This is the state which shall be reached for the determination of the enzyme activities according to the invention. For this reason the incubation is performed and is considered an essential step in the process of the invention.

The skilled person will understand that the duration of the incubation period might vary on the kind and dosage of medicament that was administered to the patient before biopsy/surgery and on the kind of biopsy or surgery influences, but that standardization to a definite period of time is plausible.

Accordingly, the minimal duration of this period should be as long as required for reaching a condition of the tissue where an influence of substrates and drugs on enzymes of the energy metabolism profile can essentially be excluded. Accordingly the incubation period, for example, can be 16 to 28 hours. Preferably an incubation period of 24 hours can be selected for the purpose of the invention. The invention suggests an incubation period of 24 hours. Most likely after that incubation time period nutrition, drug and surgery effects on the enzyme activity in the tissue slice can safely be neglected.

For the incubation of the sample or biopsy material and the tissue slices usual cell culture mediums are suited. Such cell culture mediums are commercially available. The cell culture medium RPMI 1640 is a medium that can be used for storage and transport of the sample or biopsy material and the incubation of the tissue slices. The incubation of a tissue sample to standardize the metabolic condition of the samples is an important feature of the method of the invention.

For the incubation the samples are kept under a normal atmosphere. If according to the alternative method of the invention the tissue slices shall be incubated under anaerobic or anoxic condition for reference purposes, the tissue samples can be kept under a nitrogen or carbon dioxide or a oxygen lacking atmosphere. A carbon dioxide or nitrogen atmosphere with no or substantially no oxygen is preferred. Particularly preferred is carbon dioxide.

After the incubation in a cell culture medium the tissue slices are processed to cell homogenates followed by a fractionation of the cell homogenate to cytosol and subcellular components. The preparation of cell homogenate is carried out in a disintegration buffer with an apparatus suited for gentle cell disruption. For this purpose a potter tissue grinder for tissue and cell homogenization can be used. It is important that cell walls but not mitochondrial membranes break open. Such apparatuses are described in Nature Protocols 7, 1235-1246 (2012) and are, for example, available from Sartorius AG, Germany. For example, tissue slices of tumor tissue can be broken up with a Potter-Elvehjem homogeniser. A suited disintegration buffer is, for example, a so-called buffer A, consisting of 250 mM sucrose, 50 mM KCl, 5 mM $MgCl_2$, 20 mM Tris/HCl, and water at pH 7.4 by twelve crushes without harming the integrity of the mitochondria. Mitochondria and cytosol can be accumulated by a differential centrifugation (600 g 5 minutes, supernatant 10,000 g, 10 minutes, the pellet is the mitochondrial fraction, the supernatant is the cytosolic fraction). In case of limited amounts of sample, tissue or cell homogenates can be used for measurement of enzyme activities. These homogenates can be gained by mechanical (i.e. potter tissue grinder or sonication) or chemical (i.e. detergents) cell disruption.

The enzyme activities can be measured by known and well described reactions based on the reactions mentioned above. Such reactions have been described in textbooks before. Subsequently possible concentrations of reagents for the determination of enzyme activity of a group of key enzymes of the energy metabolism are indicated.

| Enzyme | Buffer A with the additives: | Enzyme (Sigma-Aldrich) | Measurement principle |
|---|---|---|---|
| Hexokinase | 1 mM glucose 0.5 mM NADP 1 mM ATP | glucose-6-phosphatedehydrogenase Stock 2 U/mL | NADP-reduction |
| Malate decarboxylase | 2 mM malate 0.5 mM NADP | | NADP-reduction |
| Pyruvatekinase low affinity | 10 mM PEP 1 mM ADP 0.5 mM NADH | Lactate dehydrogenase Stock 6 U/mL | NADH-oxidation |
| Pyruvatekinase high affinity | 0.1 mM PEP 1 mM ADP 0.5 mM NADH | Lactate dehydrogenase 6 U/mL | NADH-oxidation |
| Lactate dehydrogenase | 1 mM pyruvate 0.5 mM NADH | | NADH-Oxidation |

| Enzyme | Buffer A with the additives: | Enzyme (Sigma-Aldrich) | Measurement principle |
|---|---|---|---|
| Complex IV | 120 mM KPi 0.05% Laurylmaltoside | 3 µl reduced Cytochrom c (5 mM) per well | Oxidation of reduced cytochrom c |

Determination of Complex IV is performed at 25° C., 96 well-plate for 10 minutes at 540-550 nm; determination of the remaining enzymes in 96 well-plate at 37° C. for 30 minutes (simultaneous) at 340-400 nm, photometer type SPECTRAmax® PLUS 384 Molecular Devices.

For the determination of the complex IV activity cytochrome c in reduced form is oxidized. To provide reduced cytochrome c as substrate for the aforementioned oxidation reaction cytochrome c is treated with a sodium dithionite solution. For example 2.7 ml of cytochrome c (oxidized) stock solution can be treated with 0.3 ml 1 M sodium dithionite solution. This stock solution can be stored in a 20 mM phosphate buffer which is kept under a nitrogen atmosphere. For the purification of the stock solution Econo®-Pc 10DG columns can be used.

In a particular preferred embodiment of the invention the reagents needed for the enzyme activity determination are deposited as solids at the bottom and/or wall of the well-plates. Well-plates treated that way allow the addition of the sample in a sample buffer and the photometric measurement of the activity of different enzymes of the samples in the wells of the plate.

Well-plates with the solid reagents deposited to the wall and/or bottom of the wells can be obtained, for example, by treatment of the wells of a well plate with a certain amount of a buffer solution with the reagents needed for the determination of enzyme activity in a suited concentration. Under vacuum the wells treated that way can be dried at a low temperature to evaporate the water of the buffer solution. The dried reagents for the determination of enzyme activity of a specific enzyme adhere to the bottom and the wall of the well.

The next step in the methods of the invention is generating the quotient of the specific enzyme activities in the tumor tissue sample and the tumor distant tissue sample or in the normoxic tumor tissue (cell mass) and the anoxic tumor tissue (cell mass).

If, for example, one considers the enzyme activities of the enzymes ME1, LDH, PKLA as anaerobic enzymes and the aerobic enzymes PKHA, COX, in each of a tumor tissue and a tumor distant tissue of one patient, one first forms the quotients of the measured enzyme activities ME1/ME1, LDH/LDH, PKLA/PKLA PKHA/PKHA and COX/COX and, as a next step, puts them into relation (ratio) to each other as shown in the following equation:

$$\frac{ME1 + LDH + PKLA}{COX + PKHA}$$

The value obtained from this equation is indicative of the formation of metastases in a patient. Both very high and very low values might reflect a poor prognosis, whereas intermediate values reflect a favorable prognosis.

Alternatively, in the case where a tumor distant tissue is not available for the generation of the aforementioned quotient the specific enzyme activity under norm oxygen condition is compared with the specific enzyme activity under maximum anaerobic condition and is expressed as a percentage value. Hence, the specific enzyme activity in the tumor tissue sample under maximum anaerobic conditions is considered being 100%. On the basis of the 100% value the percentage value of the specific enzyme activity obtained after incubation without adjusting an anaerobic condition (regular oxygen content) in the tumor tissue sample is calculated. Hence, also in this alternative method a quotient is formed of the enzyme activity measure in the presence of oxygen and without oxygen. The quotients are put in an equation as shown above. The resulting value (ratio) is indicative of the prognosis including the prediction of the likelihood of the formation of metastases, relapse or local recurrence in a patient.

For the evaluation of the patient's pathological situation a cut-off value can be advantageous. The so-called cut-off value is obtained from the statistical analysis of a large patient cohort (500 and more patients) under consideration of the quotients or results of the methods of the invention.

Subsequently the invention is further explained on the basis of the Figures and Table disclosed herein. In Table 1 the N state means patients with lymph node and/or distant metastasis (N≥1) and without metastasis (N0).

For the data presented in Table 1 the specific enzyme activity of key enzymes of all essential energy metabolisms in a cell were measured. The ME1-activity provides data on glutaminolysis. With the LDH activity data of the last reaction step in the anaerobic glycolysis and in the anaerobic glutaminolysis are provided. PKLA activity provides data on the anaerobic branch of glycolysis. PKHA activity provides data on the aerobic branch of the glycolysis and COX activity provides data on the oxidative phosphorylation (mitochondrial oxygen consumption).

Table 1 shows the measured data of all combinatory possible ratios of the anaerobic enzymes (ME1, LDH, PKLA) in relation to the aerobic enzymes (PKHA, COX). The ratio of anaerobic to aerobic energy gain in colon cancer patients with N status ≥1 is significantly increased (#15, #17-18, #20 and #26) as shown by the t-test values of the absolute (diff) or relative (ratio) difference. This is plausible.

A risk evaluation is possible on the basis of the measured values and on the basis of the calculated level of significance already with a quotient, for example, in which ME1 enzyme and at least one enzyme of the measured anaerobic and aerobic energy metabolism is included (#20 and #26).

In summary, one may conclude, that the increasing anaerobic energy gain in the tissue slices significantly correlates with tumor progression while the energy metabolism in cryo biopsies (of the same patients), if at all, only allows to differ between tumor tissue and non-tumor tissue. Moreover, the values obtained from cryo biopsies show a decrease of the anaerobic (#6, #8-9, #11-12, #14-15, #17-18, #20-21, #23-24 and #26) or aerobic (#4, #5) energy gain with increasing tumor progression what, based on the general knowledge of tumor biology, is not possible. The reason for this inability of the measurements in the cryo tissue slices to differ between the N0 and ≥N1 state on the basis of its energy profile can be a lack of standardisation in the measurement method.

According to the invention the tissue slices metabolise under strictly standardised conditions (diffusion active cut thickness of 300 µm, RPMI medium, 37° C., 5% $CO_2$, 24 h incubation time) while samples taken from cryo biopsies immediately before the measurement of enzyme activity can suffer from deeply different individual substrate offer and diverse further strongly variable influences such as food habits, chronic diseases, season, age, gender and hormone state in the body of the respective patients. The measurements show that only a standardised sample treatment and measurement process allows a significant prognosis of the progression risk of carcinoma that on the basis of the knowledge of tumors biologically makes sense.

The following abbreviations are used in Table 1: N=regionary lymph node state according to TNM classification of WHO (7$^{th}$ edition), mean=mean value, SD=standard derivation, n=number of patients, p-values (probability) <0.05 were considered statistically significant (paired T-test, two-tailed, type 2, used software: Excel®). ME1: malic enzyme 1, LDH: Lactate dehydrogenase, PKLA: Pyruvate kinase low affinity (phosphorylated dimer of PK-M2), PKHA Pyruvate kinase high affinity (non phosphorylated tetramer of PK-M2), COX: Cytochrome c oxidase.

All enzyme activities are given as ratio of the respective enzyme activity of the tumor and the tumor distant colon tissue in Table 1. This shall serve to consider potential differences in metabolism of individual patients and to consider the statistic influence of an enzyme with generally lower specific activity.

FIG. 1 shows a graphic presentation of the values of sample #26 of the Table 1. These are the quotients obtained from tumor and tumor distant tissue of a patient and of the enzyme activities of enzymes of aerobic and anaerobic energy metabolism. In one group the enzyme activity data are obtained from tissue slices according to the method of the invention after 24 hours of incubation. In the other group enzyme activities are measured in the same way, but the tissue slice is a cryo biopsy tissue without the 24 hours incubation. FIG. 1 shows that with view to discrimination between the N0 (no lymph node metastasis) and ≥N1 (lymph node metastasis present) state in colon cancer patients the data obtained according to the invention is superior to that obtained from cryo biopsy. In a tumor with lymph node metastasis the energy gain is increasingly anaerobic. This however is not established in the ratio of anaerobic/aerobic energy metabolism for the cryo biopsy tissue samples in FIG. 1, because of the high p values as compared to the p values of the fresh tissue samples conditioned according to the process of the invention.

Figure 2:
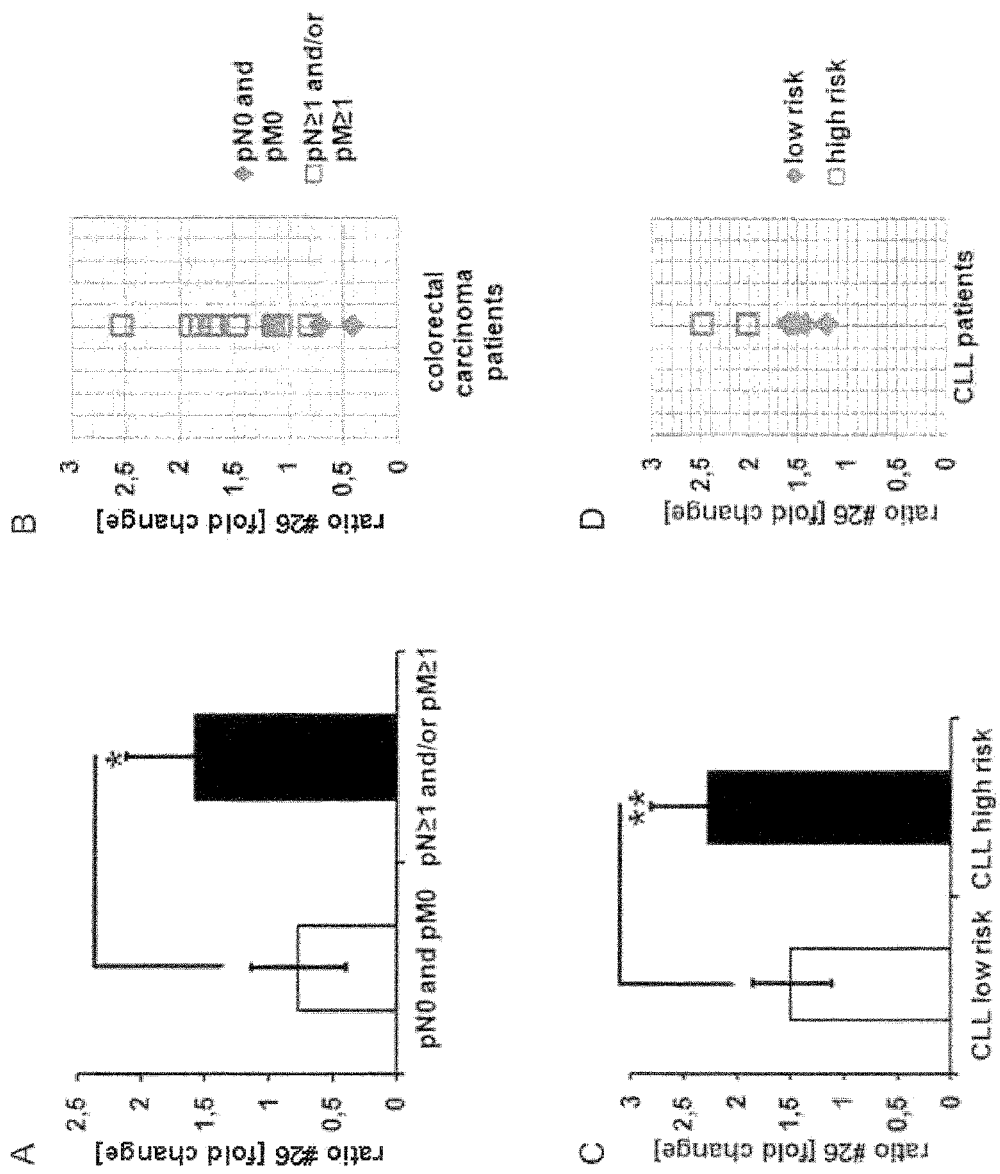
FIG. 2 is a graphical representation comprising graphs A, B, C and D for the example of FIG. 1 showing the quotients of anaerobic and aerobic energy metabolism without a normal tissue reference for patients with colon carcinoma (12 patients) and chronic lympocytic leukemia (7 patients).

FIG. 2 shows a graphic presentation of the individual quotients of the anaerobic and aerobic energy metabolism without a normal tissue as reference of eleven patients with a colon carcinoma and of seven patients with chronic lymphocytic leukemia using ratio #26 of table 1. The enzyme activities (mU/mg protein) of the indicated enzymes were measured under regular oxygen content and under anoxic condition. The anoxic condition was established by incubation of the tissue samples in $CO_2$ containing bags over a time period of 2.4 hours. An individual quotient from the enzyme activity measured in an anaerobic tissue sample and in a tissue sample incubated in the presence of regular oxygen content was formed. The graphic presentation shows the measured values under regular oxygen content as part (fold change) of the value obtained under an anoxic condition. The mean value for colorectal carcinoma patients (without lymph node and without distant metastasis) reaches 0.77±0.36 (fold change) and the mean value of colorectal carcinoma patients (with lymph node and/or distant metastasis) reaches 1.57±0.54 (fold change) of the maximum individual reference value obtained under anoxic condition of the tissue samples (FIG. 2 A, n=11, p=0.04; T-test, double-sided, type 2, software: Excel®). FIG. 2 B shows the distribution of the individual patient scores for colorectal carcinomas (n=11).

The mean value for chronic lymphocytic leukemia patients (without high risk factors: inactivating TP53 mutation and/or del(17p) and/or refractory to current standard therapies and/or short remission (<2 years)) reaches 1.49±0.16 (fold change) and the mean value of chronic lymphocytic leukemia patients (with high risk factors: inactivating TP53 mutation and/or del(17p) and/or refractory to current standard therapies and/or short remission (<2 years)) reaches 2.28±0.33 (fold change) of the maximum individual reference value obtained under anoxic condition of the tissue samples (FIG. 2 C, n=7, p=0.006; T-test, double-sided, type 2, software: Excel®). FIG. 2 D shows the distribution of the individual patient scores for chronic lymphocytic leukemia (n=7). Hence, this method is suited for the purposes of the invention where no corresponding normal tissue is present as a reference sample.

Subsequently, the invention and its application to a patient is further explained in the following examples. It should be understood that these examples are for illustrative purposes only and are not to be construed as limiting this invention in any manner.

Example 1

Therapy Recommendation for a Colon Carcinoma Patient (Patient A) in the UICC Stage II without Risk Factors after Curative Colon Carcinoma Resection on the Basis of his Metabolic Energy Profile According to the S3 guidelines "Kolorektales Karzinom" 2004/2008 (results of the evidence based consensus conferences 6-7 Feb. 2004 and 8-9 Jun. 2007, "S3 guideline "Colorectal Cancer" 2004/2008) it is possible to perform an adjuvant chemotherapy with a patient having a curative resected colorectal carcinoma in stage II (recommendation degree 0, evidence 1b, strong consensus). However, an obligatory use of an adjuvant (postoperative) chemotherapy in this stage can presently not be derived from the present randomised studies. Accordingly, in the present case the recommendation is that a therapy should at least be taken into account and that it should be discussed individually. This means that currently health professionals are not sure, whether to select a therapy option at all and if yes which therapy option shall be selected and how the prognosis for such patients might be. As risk factors in the UICC stage II a T4 stage, a tumor perforation or a tumor laceration, a surgery under emergency conditions and a too limited number of examined lymph nodes are defined. Patient A is encoded with the TNM classification pT3, pN0 (0/31), G2, R0 and according to the S3 guidelines such patient is not in a risk situation.

Colon cancer tissue and tumor distant colon tissue of such patient were subjected to the method of the invention and the following enzyme activities were determined (measurements were carried out under normoxic conditions): tumor distant colon tissue: COX=3.55 mU/mg, LDH=245 mU/mg, ME1=0.84 mU/mg, PKLA=226 mU/mg, PKHA=43 mU/mg; colon cancer tissue: COX=0.93 mU/mg, LDH=220 mU/mg, ME1:1.2 mU/mg, PKLA=211 mU/mg, PKHA=29 mU/mg; quotient (ME1+LDH+PKLA)/(COX+PKHA)= 3.50.

With parallel determinations of enzyme activity according to the alternative method of the invention the following values were obtained under anoxic conditions in colon cancer tissue: COX=2.29 mU/mg, LDH=565 mU/mg, ME1=2.74 mU/mg, PKLA=528 mU/mg, PKHA=109 mU/mg, the ratio (ME1+LDH+PKLA)/(COX+PKHA) is 1.83.

Accordingly, the ratio based on the tumor distant colon of anaerobic to aerobic energy metabolism is 3.50. Taking into account the selected enzyme combination of this example for the determination of the quotient a value of 1.50 corresponds to an equal balance between anaerobic and aerobic energy metabolism (numerator=1.0+1.0+1.0; denominator=1.0+1.0; quotient is 1.5). On the basis of his normal tissue the ratio of anaerobic to aerobic energy metabolism is more than 2.3 fold higher in the tumor tissue of patient A. On the basis of his anoxically treated tumor tissue the ratio of anaerobic to aerobic energy metabolism of patient A is more than 1.2 fold higher. If one takes into account cut-off values for the method performed with the tumor distant normal tissue of 3.0 (values ≥3.0 are associated with a worse prognosis) and of 1.0 for the method with the anoxically treated tumor tissue (values ≥1.0 are associated with a worse prognosis), the result of both methods of the invention for patient A is associated with a worse prognosis.

Based on the invention the therapy recommendation for patient A consequently is the application of an adjuvant Oxaliplatin containing chemotherapy. This therapy is obligatory for UICC stage III patients. The UICC stage III patients formally have a worse prognosis as compared to the evaluation of patient A according to the presently valid guidelines. Hence, based on the result of the method of the invention the therapy for patient A should be according to the chemotherapy protocol S3 guidelines for UICC stage III patients since, in spite of the fact that no lymph node metastases at the time of surgery and in spite of the fact that according to the guidelines the risk factors of this patient are low, in fact this patient has to expect metastasis or a relapse with a finally lethal course.

Both cut-off values are selected as examples but are realistic.

Example 2

Prognosis and Therapy Recommendation for a Symptomatic CLL (Chronic Lymphocytic Leukemia) Patient (Patient B) on the Basis of her Metabolic Tumor Energy Profile Patient B was first diagnosed with a symptomatic CLL in 1994. Since that time the patient did not show any symptoms. According to the guidelines at that time (http://www.dgho-onkopedia.de/de/onkopedia/leitlinien/cll) an observant behaviour was selected instead of a therapy as long as no symptoms occured ("w&w", "wait and watch"). Since then molecular cytogenetic FISH (fluorescence in situ hybridisation) based deletion analysis for a deletion of 17p13 and TP53 mutation analysis were negative. Patients with a 17p13 deletion and TP53 inactivating mutation show low response rates and a shorter progression free survival and overall survival according to the CLL guidelines. In 2010 the patient was diagnosed with a rare clonal TP53 mutation (in 2.51% of the tumor cells) but was still unsymptomatic. At the time of the transfer of the tissue sample material of patient B for examination, the patient had become clinically symptomatic.

In this case the alternative method of the invention with additional enzyme activity measurements under anoxic conditions was performed, since this tumor does not allow obtaining the corresponding normal cells. $2 \times 10^7$ tumor cells were purified according to a standard procedure with Ficoll® gradients from a blood sample of the patient and were provided for examination in RPMI-1640 cell culture medium. Parallel the hospital performed chromosomal aberration analysis, deletion analysis and gene mutation analysis with a sample material of patient B. According to the above described alternative method of the invention the following enzyme activities have been determined in the leukemia tumor cell mass (Indicated are the enzyme activities under norm oxygen content and under anoxic condition in brackets): COX=0.86 (0.71) mU/mg, LDH=89 (82) mU/mg, ME1=0.19 (0.07) mU/mg, PKLA=159 (132) mU/mg, PKHA=13 (16) mU/mg;

ratio (ME1+LDH+PKLA)/(COX+PKHA)=2.51.

Based on this analysis and in consideration of the tumor the exemplary, but realistic cut-off value is 2.0. This means values greater than 2.0 are associated with a worse prognosis; consequently the prognosis for patient B (quotient 2.51) is rather bad.

In contrast, the present CLL guidelines consider for patient B, who is clinically regarded as fit ("go go"), two therapy options, which are depending on the result of the chromosome analysis. In the case where patient B does not have a deletion of chromosome 17 (del(17p)) the so-called FCR scheme has to be selected for therapy (Fluradabin, Cyclophosphamid, Rituximab). With del(17p) an alternative therapy according to CLL guidelines should be selected. In this case the CLL guidelines recommend the administration of Alemtuzumab with subsequent allogenic blood stem cell transplantation because this therapy may allow a longer disease free survival. An inactivating TP53 mutation often accompanies a del(17p), however, an inactivating TP53 mutation without a del(17p) is rather seldom. Nevertheless an inactivating TP53 mutation on its own is associated with a very poor prognosis and lower response rates to the so-called FCR scheme. The CLL guidelines, however, do not give a clear recommendation on the preferred therapy for TP53 mutated CLL-patients.

Based on the method of the invention the recommendation for patient B is the administration of Alemtuzumab with subsequent consolidating allogenic blood stem cell transplantation. This recommendation is valid in spite of a lacking del (17p). In the case at hand the guidelines suggest a more favourable diseases progression and a better response on a therapy scheme different from the FCR-scheme. In the meantime, the clinical diagnostics for patient B revealed that a clonal expansion of the TP53-mutant leukemic cells had occurred. Finally the therapy recommendation on the basis of the method of the invention would have been conform to the CLL guidelines. This case shows that by using the method of the invention it was possible to recommend a therapy and give a prognosis corresponding to the guidelines in just 24 h. On the contrary, chromosomal diagnostics and mutation analysis (usual clinical tests) as performed with patient B take up to two weeks and are very cost intensive. Therefore, the claimed method is much cheaper and quicker.

In a small cohort of seven CLL patients it was possible to identify two patients (patient B and patient C) with an accuracy of 100% which have a rather bad prognosis. Patient C did not respond to the therapy and according to the CLL guidelines patient C has a statistic survival time of 1 to 2 years. With the method of the invention based on enzyme activity measured under norm oxygen conditions and under anoxic conditions the following values were obtained (values for anoxia in brackets): COX=1.16 (1.38) mU/mg, LDH=125 (126) mU/mg, ME1=0.25 (0.23) mU/mg, PKLA=108 (106) mU/mg, PKHA=12 (18) mU/mg; ratio (ME1+LDH+PKLA)/(COX+PKHA)=2.04.

Based on this analysis and in consideration of an exemplary selected realistic cut-off value for this tumor of 2.0 (values >2.0 are associated with a worse prognosis), the prognosis for patient C is rather bad.

For the seven examined CLL patients the average value of the quotient for patients with a verifiable good prognosis was 1.49±0.16. For patients with a verifiable rather bad prognosis (TP53 mutation or no response to therapy) the medium value of the quotient was 2.28±0.33. The statistical distinction in the difference of the medium values was highly significant with p=0.006 (p<0.05, T-test, double-sided, type 2, software: Excel®). A striking low individual quotient from anaerobic to aerobic energy metabolism is present in patient D; the value was 1.24, i.e. clearly below 2.0. The therapy recommendation for the symptomatic patient D is the FCR treatment scheme, his course of disease is rather favourable. As correlate to the measurements, according to the method of the invention, one would expect that ideally clinical chromosome and mutation analysis show no changes. In fact, the clinical analysis confirmed that of the examined CLL patients solely patient D shows not only neither the presence of a del(17p) nor a TP53 mutation, but also no chromosomal aberration at all. According to the CLL guidelines a rather favourable pathogenesis can be expected for patient D.

TABLE 1

| | | cryo biopsy | | | | | |
|---|---|---|---|---|---|---|---|
| | enzyme ratio [(mU/mg protein)/ | $N = 0$ | | $N \geq 1$ | | | |
| # | (mU/mg protein)] | mean | SD | mean | SD | p-value (diff) | p-value (ratio) | n |
| 1 | $ME1_{tu}/ME1_{co}$ | 1.23 | 0.32 | 1.46 | 0.28 | 0.44 | 0.40 | 6 |
| 2 | $LDH_{tu}/LDH_{co}$ | 1.79 | 0.98 | 2.25 | 0.19 | 0.53 | 0.43 | 6 |
| 3 | $PKLA_{tu}/PKLA_{co}$ | 1.46 | 0.56 | 2.07 | 1.06 | 0.30 | 0.70 | 6 |
| 4 | $PKHA_{tu}/PKHA_{co}$ | 1.12 | 0.46 | 2.53 | 0.84 | 0.06 | 0.09 | 6 |
| 5 | $COX_{tu}/COX_{co}$ | 0.54 | 0.20 | 0.66 | 0.69 | 0.76 | 0.83 | 6 |
| 6 | $(ME1_{tu}/ME1_{co})/(PKHA_{tu}/PKHA_{co})$ | 1.28 | 0.67 | 0.63 | 0.32 | 0.28 | 0.21 | 6 |
| 7 | $(ME1_{tu}/ME1_{co})/(COX_{tu}/COX_{co})$ | 2.56 | 1.20 | 5.38 | 6.05 | 0.37 | 0.68 | 6 |
| 8 | $(ME1_{tu}/ME1_{co})/[(PKHA_{tu}/PKHA_{co}) + (COX_{tu}/COX_{co})]$ | 0.75 | 0.22 | 0.54 | 0.35 | 0.40 | 0.33 | 6 |
| 9 | $(LDH_{tu}/LDH_{co})/(PKHA_{tu}/PKHA_{co})$ | 1.70 | 0.73 | 0.93 | 0.23 | 0.24 | 0.18 | 6 |
| 10 | $(LDH_{tu}/LDH_{co})/(COX_{tu}/COX_{co})$ | 3.82 | 2.25 | 7.22 | 7.25 | 0.39 | 0.58 | 6 |
| 11 | $(LDH_{tu}/LDH_{co})/[(PKHA_{tu}/PKHA_{co}) + (COX_{tu}/COX_{co})]$ | 1.07 | 0.49 | 0.78 | 0.31 | 0.51 | 0.45 | 6 |
| 12 | $(PKLA_{tu}/PKLA_{co})/(PKHA_{tu}/PKHA_{co})$ | 1.35 | 0.34 | 0.79 | 0.15 | 0.10 | 0.07 | 6 |
| 13 | $(PKLA_{tu}/PKLA_{co})/(COX_{tu}/COX_{co})$ | 3.23 | 2.00 | 5.10 | 3.72 | 0.44 | 0.51 | 6 |
| 14 | $(PKLA_{tu}/PKLA_{co})/[(PKHA_{tu}/PKHA_{co}) + (COX_{tu}/COX_{co})]$ | 0.85 | 0.28 | 0.65 | 0.02 | 0.36 | 0.37 | 6 |
| 15 | $[(ME1_{tu}/ME1_{co}) + (LDH_{tu}/LDH_{co})]/(PKHA_{tu}/PKHA_{co})$ | 2.99 | 1.28 | 1.56 | 0.55 | 0.22 | 0.18 | 6 |
| 16 | $[(ME1_{tu}/ME1_{co}) + (LDH_{tu}/LDH_{co})]/(COX_{tu}/COX_{co}))$ | 6.38 | 3.41 | 12.60 | 13.30 | 0.38 | 0.62 | 6 |
| 17 | $[(ME1_{tu}/ME1_{co}) + (LDH_{tu}/LDH_{co})]/[(PKHA_{tu}/PKHA_{co}) + (COX_{tu}/COX_{co})]$ | 1.82 | 0.66 | 1.32 | 0.56 | 0.44 | 0.36 | 6 |
| 18 | $[(ME1_{tu}/ME1_{co}) + (PKLA_{tu}/PKLA_{co})]/(PKHA_{tu}/PKHA_{co})$ | 2.63 | 0.90 | 1.42 | 0.17 | 0.15 | 0.11 | 6 |
| 19 | $[(ME1_{tu}/ME1_{co}) + (PKLA_{tu}/PKLA_{co})]/(COX_{tu}/COX_{co})$ | 5.79 | 3.17 | 10.48 | 9.77 | 0.39 | 0.55 | 6 |
| 20 | $[(ME1_{tu}/ME1_{co}) + (PKLA_{tu}/PKLA_{co})]/[(PKHA_{tu}/PKHA_{co}) + (COX_{tu}/COX_{co})]$ | 1.61 | 0.41 | 1.19 | 0.32 | 0.28 | 0.22 | 6 |
| 21 | $[(LDH_{tu}/LDH_{co}) + (PKLA_{tu}/PKLA_{co})]/(PKHA_{tu}/PKHA_{co})$ | 3.05 | 1.06 | 1.72 | 0.08 | 0.17 | 0.11 | 6 |
| 22 | $[(LDH_{tu}/LDH_{co}) + (PKLA_{tu}/PKLA_{co})]/(COX_{tu}/COX_{co})$ | 1.93 | 0.75 | 12.31 | 10.96 | 0.41 | 0.54 | 6 |
| 23 | $[(LDH_{tu}/LDH_{co}) + (PKLA_{tu}/PKLA_{co})]/[(PKHA_{tu}/PKHA_{co}) + (COX_{tu}/COX_{co})]$ | 1.93 | 0.75 | 1.43 | 0.29 | 0.44 | 0.41 | 6 |
| 24 | $[(ME1_{tu}/ME1_{co}) + (LDH_{tu}/LDH_{co}) + (PKLA_{tu}/PKLA_{co})]/(PKHA_{tu}/PKHA_{co})$ | 4.33 | 1.57 | 2.35 | 0.40 | 0.17 | 0.13 | 6 |
| 25 | $[(ME1_{tu}/ME1_{co}) + (LDH_{tu}/LDH_{co}) + (PKLA_{tu}/PKLA_{co})]/(COX_{tu}/COX_{co})$ | 9.61 | 5.35 | 17.70 | 17.02 | 0.39 | 0.56 | 6 |
| 26 | $[(ME1_{tu}/ME1_{co}) + (LDH_{tu}/LDH_{co}) + (PKLA_{tu}/PKLA_{co})]/[(PKHA_{tu}/PKHA_{co}) + (COX_{tu}/COX_{co})]$ | 2.68 | 0.90 | 1.97 | 0.64 | 0.39 | 0.32 | 6 |

| | | tissue slices | | | | | |
|---|---|---|---|---|---|---|---|
| | enzyme ratio [(mU/mg protein)/ | $N = 0$ | | $N \geq 1$ | | | |
| # | (mU/mg protein)] | mean | SD | mean | SD | p-value (diff) | p-value (ratio) | n |
| 1 | $ME1_{tu}/ME1_{co}$ | 1.48 | 0.52 | 1.22 | 0.34 | 0.37 | 0.40 | 11 |
| 2 | $LDH_{tu}/LDH_{co}$ | 1.25 | 0.36 | 1.53 | 0.43 | 0.33 | 0.30 | 9 |
| 3 | $PKLA_{tu}/PKLA_{co}$ | 1.10 | 0.21 | 1.37 | 0.57 | 0.40 | 0.45 | 9 |
| 4 | $PKHA_{tu}/PKHA_{co}$ | 1.71 | 1.34 | 0.82 | 0.54 | 0.21 | 0.13 | 9 |
| 5 | $COX_{tu}/COX_{co}$ | 0.69 | 0.30 | 0.48 | 0.14 | 0.23 | 0.27 | 8 |
| 6 | $(ME1_{tu}/ME1_{co})/(PKHA_{tu}/PKHA_{co})$ | 0.87 | 0.27 | 1.79 | 0.67 | 0.07 | 0.39 | 8 |
| 7 | $(ME1_{tu}/ME1_{co})/(COX_{tu}/COX_{co})$ | 2.14 | 0.73 | 2.56 | 0.34 | 0.29 | 0.12 | 8 |

TABLE 1-continued

| # | Formula | | | | | | | |
|---|---|---|---|---|---|---|---|---|
| 8 | $(ME1_{tu}/ME1_{co})/[(PKHA_{tu}/PKHA_{co}) + (COX_{tu}/COX_{co})]$ | 0.59 | 0.13 | 1.02 | 0.28 | 0.05 | 0.96 | 8 |
| 9 | $(LDH_{tu}/LDH_{co})/(PKHA_{tu}/PKHA_{co})$ | 0.88 | 0.56 | 2.23 | 1.00 | 0.08 | 0.65 | 8 |
| 10 | $(LDH_{tu}/LDH_{co})/(COX_{tu}/COX_{co})$ | 2.18 | 1.79 | 3.38 | 1.11 | 0.28 | 0.19 | 8 |
| 11 | $(LDH_{tu}/LDH_{co})/[(PKHA_{tu}/PKHA_{co}) + (COX_{tu}/COX_{co})]$ | 0.61 | 0.42 | 1.29 | 0.45 | 0.08 | 0.81 | 8 |
| 12 | $(PKLA_{tu}/PKLA_{co})/(PKHA_{tu}/PKHA_{co})$ | 0.84 | 0.47 | 1.90 | 0.84 | 0.10 | 0.75 | 8 |
| 13 | $(PKLA_{tu}/PKLA_{co})/(COX_{tu}/COX_{co})$ | 2.03 | 1.32 | 2.93 | 1.15 | 0.35 | 0.22 | 8 |
| 14 | $(PKLA_{tu}/PKLA_{co})/[(PKHA_{tu}/PKHA_{co}) + (COX_{tu}/COX_{co})]$ | 0.57 | 0.32 | 1.10 | 0.35 | 0.08 | 0.68 | 8 |
| 15 | $[(ME1_{tu}/ME1_{co}) + (LDH_{tu}/LDH_{co})]/(PKHA_{tu}/PKHA_{co})$ | 1.75 | 0.80 | 4.02 | 1.47 | 0.05 | 0.04 | 8 |
| 16 | $[(ME1_{tu}/ME1_{co}) + (LDH_{tu}/LDH_{co})]/(COX_{tu}/COX_{co}))$ | 4.31 | 2.43 | 6.94 | 1.20 | 0.24 | 0.14 | 8 |
| 17 | $[(ME1_{tu}/ME1_{co}) + (LDH_{tu}/LDH_{co})]/[(PKHA_{tu}/PKHA_{co}) + (COX_{tu}/COX_{co})]$ | 1.20 | 0.55 | 2.31 | 0.60 | 0.04 | 0.06 | 8 |
| 18 | $[(ME1_{tu}/ME1_{co}) + (PKLA_{tu}/PKLA_{co})]/(PKHA_{tu}/PKHA_{co})$ | 1.71 | 0.73 | 3.69 | 1.30 | 0.06 | 0.04 | 8 |
| 19 | $[(ME1_{tu}/ME1_{co}) + (PKLA_{tu}/PKLA_{co})]/(COX_{tu}/COX_{co})$ | 4.16 | 1.97 | 5.49 | 1.13 | 0.26 | 0.15 | 8 |
| 20 | $[(ME1_{tu}/ME1_{co}) + (PKLA_{tu}/PKLA_{co})]/[(PKHA_{tu}/PKHA_{co}) + (COX_{tu}/COX_{co})]$ | 1.16 | 0.45 | 2.11 | 0.46 | 0.03 | 0.03 | 8 |
| 21 | $[(LDH_{tu}/LDH_{co}) + (PKLA_{tu}/PKLA_{co})]/(PKHA_{tu}/PKHA_{co})$ | 1.72 | 1.03 | 4.13 | 1.80 | 0.08 | 0.05 | 8 |
| 22 | $[(LDH_{tu}/LDH_{co}) + (PKLA_{tu}/PKLA_{co})]/(COX_{tu}/COX_{co})$ | 4.20 | 3.11 | 6.30 | 2.17 | 0.30 | 0.16 | 8 |
| 23 | $[(LDH_{tu}/LDH_{co}) + (PKLA_{tu}/PKLA_{co})]/[(PKHA_{tu}/PKHA_{co}) + (COX_{tu}/COX_{co})]$ | 1.18 | 0.73 | 2.39 | 0.77 | 0.07 | 0.24 | 8 |
| 24 | $[(ME1_{tu}/ME1_{co}) + (LDH_{tu}/LDH_{co}) + (PKLA_{tu}/PKLA_{co})]/(PKHA_{tu}/PKHA_{co})$ | 2.59 | 1.27 | 5.92 | 2.22 | 0.06 | 0.05 | 8 |
| 25 | $[(ME1_{tu}/ME1_{co}) + (LDH_{tu}/LDH_{co}) + (PKLA_{tu}/PKLA_{co})]/(COX_{tu}/COX_{co})$ | 6.34 | 3.74 | 8.86 | 2.18 | 0.26 | 0.16 | 8 |
| 26 | $[(ME1_{tu}/ME1_{co}) + (LDH_{tu}/LDH_{co}) + (PKLA_{tu}/PKLA_{co})]/[(PKHA_{tu}/PKHA_{co}) + (COX_{tu}/COX_{co})]$ | 1.77 | 0.87 | 3.40 | 0.87 | 0.04 | 0.03 | 8 |

The invention claimed is:

1. A diagnostic method for the prediction of tumor prognosis including the likelihood of formation of metastases, relapse occurrence, and/or local recurrence and the provision of a therapy recommendation comprising the steps of
   (a) incubation of a tumor patient's fresh sample material and a fresh comparative sample material from the patient in a culture medium for a time sufficient to eliminate nutrition, drug and biopsy effects on the energy metabolism in the sample materials:
   (b) preparation of a cell homogenate and subcellular fractions from the sample materials of step (a);
   (c) determination of enzyme activities of at least one anaerobic key enzyme and at least one aerobic key enzyme of the energy metabolism of the cell homogenate or the subcellular fraction and determination of a quotient for each key enzyme of the enzyme activity determined in the sample material and the enzyme activity determined in the comparative sample material wherein the one or more anaerobic key enzyme is selected from the group consisting of malic enzyme (ME), lactate dehydrogenase (LDH), pyruvate kinase low affinity (PKLA), hexokinase and an acyl-CoA dehydrogenase and wherein the one or more aerobic key enzyme is selected from the group consisting of pyruvate kinase high affinity (PKHA) and cytochrome c oxidase (COX); and
   (d) calculation of a ratio of the sum of the anaerobic key enzyme quotients and the sum of the aerobic key enzyme quotients using the quotients determined in step (c) in the sample material and the comparative sample material, wherein a decrease in the ratio of aerobic to anaerobic key enzyme quotients or increase in the ratio of the anaerobic to aerobic key enzyme quotients, when compared to a value for balanced anaerobic and aerobic metabolism, correlates with tumor progression, wherein the patient sample material is selected from the group consisting of tumor tissue slices, tumor cell mass and isolated tumor cells and the comparative sample material is selected from the group consisting of a tumor distant tissue slice and a material which in step (a) is incubated under conditions that up regulate the anaerobic energy metabolism; and
   (e) selecting a method of treatment based on the calculated ratio.

2. The diagnostic method of claim 1, wherein at least two anaerobic key enzymes and at least one aerobic key enzyme are selected.

3. The diagnostic method of claim 1, wherein two anaerobic key enzymes and one aerobic key enzyme are selected, and wherein LDH and PKLA are selected as the anaerobic key enzymes and PKHA is selected as the aerobic key enzyme.

4. The diagnostic method of claim 1, said method performed in a well plate, wherein the reagents for the determination of enzyme activity are pre-deposited on walls of the wells of the well plate.

5. A diagnostic method for the prediction of tumor prognosis including the likelihood of formation of metastases, relapse occurrence, and/or local recurrence and the provision of a therapy recommendation wherein a fresh sample material comprises tissue slices from a biopsy material, comprising the steps of
   (a) incubation of the tissue slices taken from a biopsy material of a tumor tissue and of a tumor distant tissue of a patient in a culture medium for a time sufficient to eliminate nutrition, drug and biopsy effects on the energy metabolism of the tissue slices;

(b) preparation of a cell homogenate and subcellular fractions from the tissue slices of step (a);

(c) determination of enzyme activities of at least one anaerobic key enzyme and at least one aerobic key enzyme of the energy metabolism of the cell homogenate or the subcellular fraction in the tumor tissue and the tumor distant tissue and determination of a quotient for each key enzyme of the enzyme activity determined in the tumor tissue and the enzyme activity determined in the tumor distant tissue wherein the one or more anaerobic key enzyme is selected from the group consisting of malic enzyme (ME), lactate dehydrogenase (LDH), pyruvate kinase low affinity (PKLA), hexokinase and an acyl-CoA dehydrogenase; and wherein the one or more aerobic key enzyme is selected from the group consisting of pyruvate kinase high affinity (PKHA) and cytochrome c oxidase (COX); and (d) calculation of a ratio of the sum of the anaerobic key enzyme quotients and the sum of the aerobic key enzyme quotients using the quotients determined in step (c) in the tumor tissue and the tumor distant tissue, wherein a decrease in the ratio of aerobic to anaerobic key enzyme quotients or an increase in the ratio of the anaerobic to aerobic key enzyme quotients, when compared to a value for balanced anaerobic and aerobic metabolism, correlates with tumor progression; and (e) selecting a methods of treatment based on the calculated ratio.

6. The diagnostic method of claim 5, wherein at least two anaerobic key enzymes and at least one aerobic key enzyme are selected.

7. The diagnostic method of claim 5, wherein two anaerobic key enzymes and one aerobic key enzyme are selected, and wherein LDH and PKLA are selected as the anaerobic key enzymes and PKHA is selected as the aerobic key enzyme.

8. The diagnostic method of claim 5, said method performed in a well plate, wherein the reagents for the determination of enzyme activity are pre-deposited on walls of the wells of the well plate.

9. A diagnostic method for the prediction of tumor prognosis including the likelihood of formation of metastases, relapse occurrence, and/or local recurrence and the provision of a therapy recommendation wherein a fresh sample material comprises the tissue slice from a biopsy material comprising the steps of (a) incubation of the tissue slice taken from the biopsy material of a tumor tissue of a patient in a cell culture medium for a time sufficient to eliminate drug, nutrition and biopsy effects on the energy metabolism of the tissue slice;

(b) incubation of a second tissue slice from the same biopsy material under conditions that up regulate the anaerobic energy metabolism in the tissue slice;

(c) preparation of a cell homogenate and subcellular fractions from the tissue slice of step (a), (d) determination of enzyme activities of at least one anaerobic key enzyme and at least one aerobic key enzyme of the energy metabolism of the cell homogenate or a subcellular fraction in the tumor tissue sample and in the tumor tissue sample with the up regulated anaerobic energy metabolism and formation of a quotient for each key enzyme of the enzyme activity in the tumor tissue and the enzyme activity determined in the tumor tissue sample with the up regulated anaerobic energy metabolism wherein the one or more anaerobic key enzyme is selected from the group consisting of malic enzyme (ME), lactate dehydrogenase (LDH), pyruvate kinase low affinity (PKLA), hexokinase and an acyl-CoA dehydrogenase and wherein the one or more aerobic key enzyme is selected from the group consisting of pyruvate kinase high affinity (PKHA) and cytochrome c oxidase (COX); and (e) calculation of a ratio of the sum of the anaerobic key enzyme quotients to and the sum of the aerobic key enzyme quotients using the quotients determined in step (d) in the tumor tissue and in the tumor tissue sample with the up regulated anaerobic energy metabolism, wherein a decrease in the ratio of aerobic to anaerobic or an increase in the ratio of anaerobic to aerobic key enzyme quotients, when compared to a value for balanced anaerobic and aerobic metabolism, correlates with tumor progression; and (f) selecting a method of treatment based on the calculated ratio.

10. The diagnostic method of claim 9, wherein at least two anaerobic key enzymes and at least one aerobic key enzyme are selected.

11. The diagnostic method of claim 9, wherein two anaerobic key enzymes and one aerobic key enzyme are selected, and wherein LDH and PKLA are selected as the anaerobic key enzymes and PKHA is selected as the aerobic key enzyme.

12. The diagnostic method of claim 9, said method performed in a well plate, wherein the reagents for the determination of enzyme activity are pre-deposited on walls of the wells of the well plate.

13. A diagnostic method for the prediction of tumor prognosis including the likelihood of formation of metastases, relapse occurrence, and/or local recurrence and the provision of a therapy recommendation wherein a fresh sample material comprises a tumor cell mass comprising the steps of (a) incubation of a part of the tumor cell mass taken from a patient in a cell culture medium for a time sufficient to eliminate drug, nutrition and biopsy effects on the energy metabolism;

(b) incubation of a second part of the same tumor cell mass taken from the patient under conditions that up regulate the anaerobic energy metabolism;

(c) preparation of a cell homogenate and subcellular fractions from the tumor cell mass of step (a), (d) determination of enzyme activity of at least one anaerobic key enzyme and at least one aerobic key enzyme of the energy metabolism of the subcellular fraction or the cell homogenate in the tumor cell mass and in the tumor cell mass with the up regulated anaerobic energy metabolism and determination of a quotient for each key enzyme of the enzyme activity in the tumor cell mass and the enzyme activity determined in the tumor cell mass with the up regulated anaerobic energy metabolism wherein the one or more anaerobic key enzyme is selected from the group consisting of malic enzyme (ME), lactate dehydrogenase (LDH), pyruvate kinase low affinity (PKLA), hexokinase and an acyl-CoA dehydrogenase and wherein the one or more aerobic key enzyme is selected from the group consisting of pyruvate kinase high affinity (PKHA) and cytochrome c oxidase (COX); and (e) calculation of a ratio of the sum of the anaerobic key enzyme quotients and the sum of the aerobic key enzyme quotients using the quotients determined in step (d) in the tumor cell mass of step (a) and in the tumor cell mass with the up regulated anaerobic energy metabolism, wherein a decrease in the ratio of aerobic to anaerobic key enzyme quotients or an increase in the ratio of the anaerobic to aerobic key enzyme quotients, when compared to value for balanced anaerobic and aerobic metabolism, correlates with tumor progression; and (f) selecting a method of treatment based on the calculated ratio.

14. The diagnostic method of claim 13, wherein at least two anaerobic key enzymes and at least one aerobic key enzyme are selected.

15. The diagnostic method of claim 13, wherein two anaerobic key enzymes and one aerobic key enzyme are selected, and wherein LDH and PKLA are selected as the anaerobic key enzymes and PKHA is selected as the aerobic key enzyme.

16. The diagnostic method of claim 13, said method performed in a well plate, wherein the reagents for the determination of enzyme activity are pre-deposited on walls of the wells of the well plate.

17. A diagnostic method for the prediction of tumor prognosis including the likelihood of formation of metastases, relapse occurrence, and/or local recurrence and the provision of a therapy recommendation wherein a fresh sample material comprises isolated cells from a solid or liquid tumor comprising the steps of
   a) isolation of the cells from the solid or liquid tumor sample taken from a patient, estimation of the number of isolated tumor cells, dilution of the cells and incubation of the cells in a cell culture medium for a time sufficient to eliminate drug, nutrition and biopsy effects on the energy metabolism and to allow proliferation of the cells;
   (b) incubation of the same amount of cells that were isolated and treated as described in step (a) under conditions that up regulate the anaerobic energy metabolism;
   (c) preparation of subcellular fractions and a cell homogenate from the isolated tumor cells of steps (a) and (b);
   (d) determination of enzyme activity of at least one anaerobic key enzyme and at least one aerobic key enzyme of the energy metabolism of the sub cellular fraction or the cell homogenate in the isolated tumor cells and in the isolated tumor cells with the up regulated anaerobic energy metabolism and determination of a quotient for each key enzyme of the enzyme activity in the isolated tumor cells of step (a) and the enzyme activity determined in the isolated tumor cells with the up regulated anaerobic energy metabolism wherein the one or more anaerobic key enzyme is selected from the group consisting of malic enzyme (ME), lactate dehydrogenase (LDH), pyruvate kinase low affinity (PKLA), hexokinase and an acyl-CoA dehydrogenase; and wherein the one or more aerobic key enzyme is selected from the group consisting of pyruvate kinase high affinity (PKHA) and cytochrome c oxidase (COX); and
   (e) calculation of a ratio of the sum of the anaerobic key enzyme quotients and the sum of the aerobic key enzyme quotients using the quotient determined in step (d) in the isolated tumor cells of step (a) and in the isolated tumor cells with the up regulated anaerobic energy metabolism, wherein a decrease in the ratio of aerobic to anaerobic or an increase in the ratio of the anaerobic to aerobic key enzyme quotients, when compared to a value for balanced anaerobic and aerobic metabolism, correlates with tumor progression; and (f) selecting a method of treatment based on the calculated ratio.

18. The diagnostic method of claim 17, wherein at least two anaerobic key enzymes and at least one aerobic key enzymes are selected.

19. The diagnostic method of claim 17, said method performed in a well plate, wherein the reagents for the determination of enzyme activity are pre-deposited on walls of the wells of the well plate.

20. The diagnostic method of claim 17, wherein two anaerobic key enzymes and one aerobic key enzyme are selected, and wherein LDH and PKLA are selected as the anaerobic key enzymes and PKHA is selected as the aerobic key enzyme.

21. The diagnostic method of claim 17, said method performed in a well plate, wherein the reagents for the determination of enzyme activity are pre-deposited on walls of the wells of the well plate.

22. A method for predicting tumor prognosis comprising the likelihood of formation of metastases, relapse occurrence, and/or local recurrence and based thereon providing alternative therapeutic treatments said method comprising
   (a) incubating material from a fresh tumor sample obtained from a patient and a comparative fresh sample material from the patient in a culture medium for a time sufficient to eliminate nutrition, drug and biopsy effects on the energy metabolism in the sample materials;
   (b) preparing a cell homogenate and subcellular fractions from the sample materials of step (a);
   (c) determining the enzyme activities of at least one anaerobic key enzyme and at least one aerobic key enzyme of the energy metabolism of the cell homogenate or the subcellular fraction in the patient's fresh tumor sample and in the patient's comparative fresh sample, and determining a quotient for each key enzyme of the enzyme activity determined in the patient's tumor sample and the enzyme activity determined in the patient's comparative sample; wherein the one or more anaerobic key enzyme is selected from the group consisting of malic enzyme (ME), lactate dehydrogenase (LDH), pyruvate kinase low affinity (PKLA), hexokinase and an acyl-CoA dehydrogenase and wherein the one or more aerobic key enzyme is selected from the group consisting of pyruvate kinase high affinity (PKHA) and cytochrome c oxidase (COX); and
   d) calculating a ratio of the sum of the anaerobic key enzyme quotients and the sum of the aerobic key enzyme quotients using the quotients for each key enzyme determined in step (c) in the sample material and the comparative sample material, wherein a decrease in the ratio of aerobic to anaerobic key enzyme quotients or an increase in the ratio of the anaerobic to aerobic key enzyme quotients, when compared to a value for balanced anaerobic and aerobic metabolism, correlates with tumor progression, where the tumor sample material is selected from the group consisting of tumor tissue slices, tumor cell mass and isolated tumor cells and the comparative sample material is selected from the group consisting of a slice of tissue from a distant tumor or a material which in step (a) is incubated under conditions that up-regulate the anaerobic energy metabolism; and
   (e) selecting a method of treatment based on the calculated ratio.

23. The diagnostic method of claim 22, wherein at least two anaerobic key enzymes and at least one aerobic key enzyme are selected.

24. The diagnostic method of claim 22, wherein two anaerobic key enzymes and one aerobic key enzyme are selected, and wherein LDH and PKLA are selected as the anaerobic key enzymes and PKHA is selected as the aerobic key enzyme.

* * * * *